United States Patent [19]

Augustine

[11] Patent Number: 5,042,469

[45] Date of Patent: * Aug. 27, 1991

[54] TRACHEAL INTUBATION GUIDE

[75] Inventor: Scott D. Augustine, Bloomington, Minn.

[73] Assignee: Augustine Medical, Inc., Eden Prairie, Minn.

[*] Notice: The portion of the term of this patent subsequent to May 23, 2006 has been disclaimed.

[21] Appl. No.: 356,295

[22] Filed: May 22, 1989

Related U.S. Application Data

[63] Continuation-in-part of Ser. No. 126,567, Nov. 30, 1987, Pat. No. 4,832,020, which is a continuation-in-part of Ser. No. 30,697, Mar. 24, 1987, abandoned.

[51] Int. Cl.$^5$ .............................. A61M 16/00
[52] U.S. Cl. ........................ 128/200.26; 128/207.14
[58] Field of Search .................. 128/200.26, 207.14, 128/10, 207.15, 3; 604/264

[56] References Cited

U.S. PATENT DOCUMENTS

| | | | |
|---|---|---|---|
| 2,354,471 | 7/1944 | Macintosh | 128/10 |
| 3,802,440 | 4/1974 | Salem et al. | 128/351 |
| 3,986,854 | 10/1976 | Scrivo et al. | 128/16 |
| 4,067,331 | 1/1978 | Berman | 128/200.26 |
| 4,356,821 | 11/1982 | Rind | 128/207.14 |
| 4,432,351 | 2/1984 | Hoary | 128/3 |
| 4,612,927 | 9/1986 | Krüger | 128/200.26 |
| 4,669,463 | 6/1987 | McConnell | 128/207.14 |
| 4,712,536 | 12/1987 | Hawks | 128/3 |
| 4,713,053 | 12/1987 | Lee | 604/264 |
| 4,832,020 | 5/1989 | Augustine | 128/207.14 |

FOREIGN PATENT DOCUMENTS 0086850 8/1983 European Pat. Off. .

OTHER PUBLICATIONS

European Search Report, dated 9/5/89 for 88302478.8.

Primary Examiner—Edgar S. Burr
Assistant Examiner—E. P. Raciti
Attorney, Agent, or Firm—Baker, Maxham, Jester & Meador

[57] ABSTRACT

A tracheal intubation guide comprises a tubular member having a curved forward end shaped to follow the curvature of the back of the tongue and throat of a patient, and a rear end for projecting out through the mouth of the patient, and an anterior guide surface extending along at least part of the length of the member to its forward end for guiding the member into the throat into a position opposite the opening into the larynx. The tubular member has a through bore for holding an endotracheal tube, and the guide surface has a forward edge of concave shape for engaging the front of the epiglottis and seating over the hyo-epiglottic ligament when the member is accurately positioned. Correct positioning can be detected by external palpation of the neck.

10 Claims, 5 Drawing Sheets

TRACHEAL INTUBATION GUIDE

RELATED PATENT APPLICATIONS

This patent application is a continuation-in-part of U.S. patent application Ser. No. 07/126,567, filed Nov. 30, 1987, now U.S. Pat. No. 4,832,020, issued May 23, 1989, which was a continuation-in-part of U.S. patent application Ser. No. 030,699, filed on Mar. 24, 1987, and now abandoned.

BACKGROUND OF THE INVENTION

The present invention relates to a guide for assisting medical personnel in inserting an endotracheal tube into the trachea, or windpipe, of a patient.

Endotracheal intubation is the technique of inserting a tube into the trachea of a patient in order to aid in or permit respiration. It is commonly used in surgery and in emergency care situations, for example, in the case of trauma or cardiac arrest victims suffering from breathing difficulties. Various other techniques for securing an airway are known, such as the esophageal obturator airway, the esophageal gastric tube airway, and the pharyngeal tracheal lumen airway, as well as mouth to mouth or bag and mask respiration. However, none of these places an airway into the trachea, and, thus, none of them will truly secure the airway to prevent potential aspiration of blood, vomitus, or other foreign material into the lungs. Additionally, some of these techniques can induce major additional trauma in the patient.

Thus, endotracheal intubation is generally considered to be the superior method of securing an airway and assuring adequate ventilation. However, one problem with this technique is that it requires significant operator skill and experience. Unskilled insertion can cause additional injuries, for example, to the front incisors. Another problem is that many existing techniques for inserting a tube into the trachea require special positioning of the patient's head, and thus cannot be done with trauma victims until cervical spine fractures have been ruled out, because of the possibility of additional spinal cord damage.

A laryngoscope is commonly used to aid in placing of an endotracheal tube. This allows the operator to observe the insertion of the tube, but requires that the patient be positioned with their head tilted back, which is not normally possible with trauma victims. Visualization of the larynx may be impossible if the pharynx is filled with blood or vomitus. Laryngoscopes are relatively difficult instruments to handle, even for skilled medical personnel. Thus, they are not normally suitable for use by paramedical personnel in the field.

Other endotracheal intubation techniques involve the insertion of the tube "blind" or by feel. Some devices have been proposed in the past for aiding in "blind" insertion of an endotracheal tube. U.S. Pat. No. 4,612,927 of Kruger, for example, shows an instrument of open channel section terminating in a head having a central concavity for engaging the rear of the larynx. A tube can then be guided along the channel and directed into the trachea via a suitable ramp adjacent the head of the instrument. U.S. Pat. Nos. 4,054,135, 4,068,658, 4,067,331, and 4,069,820 of Berman all show a pharyngeal airway for intubation which has a distal tip for engaging the epiglottis to direct a tube into the trachea.

SUMMARY OF THE INVENTION

It is an object of the present invent to provide an improved guide for endotracheal intubation, which can permit medical personnel, with suitable training, to insert a tube into the trachea relatively easily.

According to the present invention, an endotracheal intubation guide is provided which comprises a tubular member having a curved forward end shaped to follow the curvature of the back of the tongue and anterior surface of the throat of a patient and a rear end for projecting out through the mouth of the patient, and an anterior guide surface which extends along at least part of the length of the tubular member to its forward end and is of equivalent curvature, for guiding the tubular member into the mouth and throat of a patient. The guide surface has a forward edge of concave shape for engaging the front of the epiglottis and for seating over the hyo-epiglottic ligament to position the tubular member opposite the opening to the larynx. When the guide has been inserted through a patient's mouth until the front edge of the guide surface is accurately seated, an endotracheal tube previously inserted through the tubular member towards its forward end can be advanced into the trachea.

Accurate positioning of the guide can be detected by external palpation of the neck of the patient. The epiglottis is a shield-shaped cartilage which rises above the opening to the windpipe or larynx. The epiglottis is anchored anteriorly to the hyoid bond in its midline by the hyo-epiglottic ligament. The hyoid bone is the highest bone palpable on the anterior aspect of the neck, and is a U-shaped structure which surrounds and suspends the larynx (the upper end of the windpipe). The epiglottis is always on the anterior, superior aspect of the larynx, and the guide of this invention uses this relationship to establish accurate positioning of an endotracheal tube.

According to another aspect of the present invention, a method of inserting an endotracheal tube comprises the steps of first inserting the endotracheal tube from the rear to the forward end of the intubation guide. The guide is then inserted through the mouth and throat of the patient. The guide surface travels over the tongue and anterior surface of the throat until its forward edge engages the front of the epiglottis. Accurate, central positioning of the guide surface can be detected by external palpation of the neck at and above the hyoid bond. If the guide is not accurately positioned with the concave edge centrally seated on the ligament in the midline, a lateral edge of the guide would be palpable on one or the other side of the neck above the hyoid bone, requiring re-positioning of the guide. Accurate midline positioning with the concave edge of the guide surface seated on the hyo-epiglottic ligament can be detected by lateral movements of the guide which will be detected externally as a generalized movement of the hyoid bone, felt by palpation of the neck in the area of the bone. Once accurate positioning is detected, anterior elevation of the tongue will tension the hyo-epiglottic ligament and elevate the epiglottis anteriorly, opening the larynx immediately posterior to the epiglottis. The guide tube member will then be positioned with its open forward end directly opposing the opening to the larynx. The endotracheal tube can then be advanced through the forward end of the guide member and into the larynx and trachea. At this point, the guide can be removed, leaving the endotracheal tube in place.

The anterior guide surface may be formed integrally with the tubular guide member or may be a generally flat, J-shaped member secured to the anterior surface of the tubular member. The forward edge of the guide surface preferably projects forwardly of the open forward end of the tubular member. In a first embodiment of the invention, a pair of rollers are mounted at the forward edge of the guide surface, and the concave shape is defined by the opposed faces of the rollers which are designed to seat around the hyo-epiglottic ligament when the guide is accurately positioned. The rollers aid in sliding the guide over the rear of the tongue of a patient, which can be sticky in some patients. Additional rollers may be provided along the curved portion of the guide surface to facilitate sliding movement of the tracheal intubation guide. In a second embodiment of the invention, the guide surface is smooth and unbroken with the concave shape at the forward edge of the guide surface being defined by a pair of curved projections which are designed to seat around the hyo-epiglottic ligament. In the second embodiment, the guide slides adequately over the rear of the patient's tongue.

The tubular member itself preferably has portions of open section to aid in removal of the guide once an endotracheal tube has been inserted. The open portions are preferably provided by a continuous, serpentine cut-out extending along the length of the tube which is designed so that an endotracheal tube will be kept within the tubular member during positioning but allows the guide to be easily removed once the tube is advanced into the trachea. A suitable handle may be provided at the rear end of the guide for holding by an operator while inserting the guide, and a thumb indent may be provided on the handle to ensure alignment of the tubular member with the operator's hand, which assists in accurate positioning of the guide on insertion.

From yet another aspect, tracheal intubation according to the present invention is accomplished by a tracheal intubation guide which facilitates insertion of a tube into the trachea of a patient, and which includes a tubular member with proximal and distal ends and having a substantially straight proximal section which includes the proximal end, a distal section which includes the distal end, and a curved section joining the proximal and distal sections. A blade edge is provided in the distal end which includes a centering, hyo-epiglottic ligament engagement indentation. A pair of bulbous hyoid engagement projections are provided on the blade edge, each of the projections being displaced in a respective lateral direction from the indentation. An anterior tongue-engagement surface extends along the elongate tubular member, and a continuous tube disengagement opening is provided in the tubular member which extends from the distal end to the proximal end. The tube disengagement opening includes a portion in the curved section which opens opposite the tongue-engagement surface.

In this last aspect, the invention includes a method for intubation of a patient's trachea, which method is practiced by means of a tracheal intubation guide with distal end, a proximal end, a curved anterior surface, means for releasibly retaining a tube, and hyoid engagement means on the distal end. The method has the steps of, first, inserting a tube into the tracheal intubation guide, and then inserting the tracheal intubation guide, distal end first, into a patient's mouth, so that the guide surface follows the rear surface of the tongue into the throat. Next, the tracheal intubation guide is advanced until the distal end hyoid engagement means engages the hyoid bone. Then, accurate positioning of the tracheal intubation guide is detected by palpation of the sides of the neck to determine whether the hyoid bone has been elevated. In addition to these steps, the method further includes the steps of applying lateral motion to the tracheal intubation guide at the proximal end and palpating the sides of the neck to determine whether the hyoid bone is moved laterally. Then, the epiglotis is elevated anteriorly to open the larynx, the tube is guided into the trachea, and the tracheal intubation guide is removed from the tube and the patient's mouth.

The tracheal intubation guide and method of this invention will aid in accurate intubation of the trachea, increasing the reliability and safety of this procedure. It is particularly useful in the case of trauma or other emergency victims, where use of a laryngoscope may not be possible, since it does not require movement of the head, or visualization of the larynx.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 1:
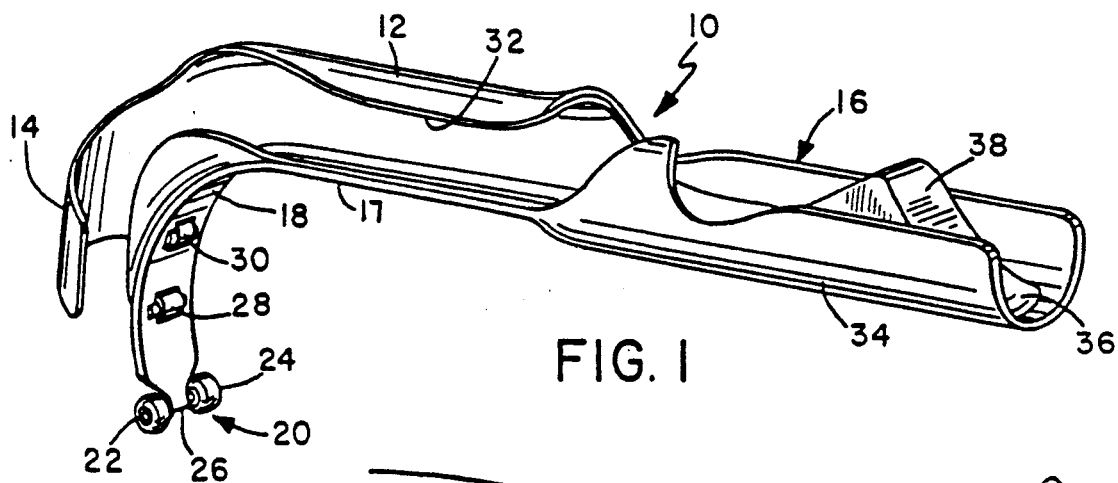
FIG. 1 is a perspective view of a tracheal intubation guide according to a first embodiment of the invention.
Figure 2:
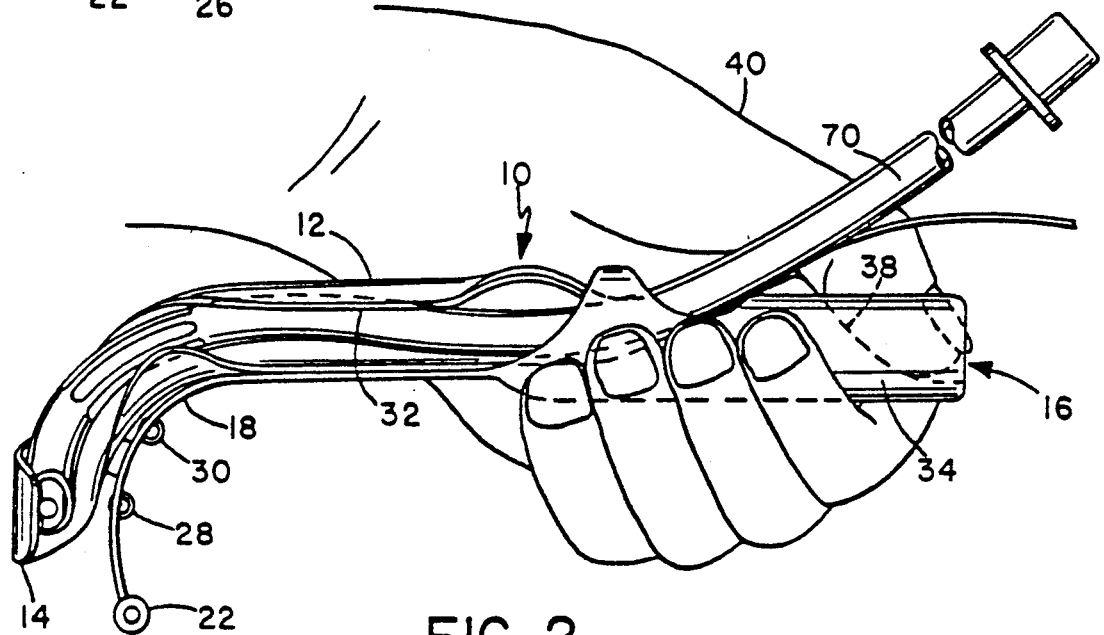
FIG. 2 is a side elevation view of the first embodiment guide with an endotracheal tube inserted and showing the method of holding the guide.

FIGS. 1 and 2 of the drawings show a tracheal intubation guide 10 according to a first embodiment of the present invention. The guide 10 basically comprises a tubular member or guide tube 12 having a curved forward end 14 and a generally straight rear end 16, an underside 17, and an anterior guide surface 18 extending along at least part of the length of the underside of the tubular member and beyond the tubular member's forward end. The guide surface 18 may be formed integrally with the tubular member or may be suitably attached to the anterior surface of member 12, and is suitably a generally flattened J-shaped strip as seen in FIGS. 1 and 2. In one example, the strip was approximately ¾ inch wide, although other dimensions may be appropriate for different age patients.

As can be seen in FIG. 1, the forward edge 20 of the guide surface 18 is of generally concave shape, the concave shape in the first embodiment being defined between a pair of rollers or wheels 22, 24 which have suitably inclined opposing faces to define a concave shape or indent 26. The rollers 22,24 are preferably of rounded, ball-like shape as shown in FIG. 1. An additional pair of rollers 28, 30 are provided along the curved portion of the guide surface 18.

The tubular member 12 has open portions along its length, and in the first embodiment of the invention member 12 has a serpentine slot or cutout 32 extending along it. A suitable handle 34 is provided at the rear end of member 12 for holding of the guide by an operator as illustrated in FIG. 2. The handle has a suitable thumb indent 36 comprising a ramped surface 38 at its outer end for positioning of the operator's thumb 40 while holding the guide as shown in FIG. 2. This ensures that the guide 10 is aligned with the operator's hand during insertion. The guide 10 is preferably held by the operator in a similar manner to a traditional laryngoscope, with the operator positioned at the patient's head.

The guide is rigid, and may be of any suitable non-toxic material such as a plastics material. The curvature of the forward end of the guide is designed to follow the general curvature of the back of the tongue and anterior surface of the throat, as explained below.

Figure 5:
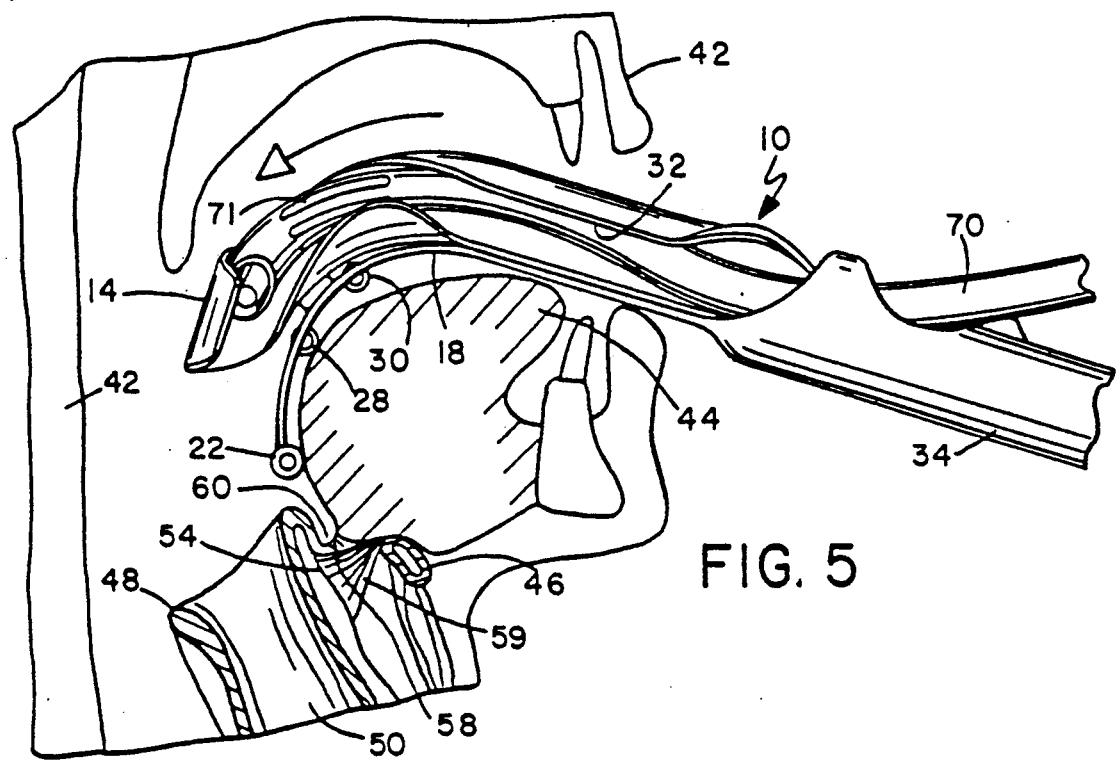
FIG. 5 is a cutaway view of a mouth and throat area, showing insertion of the first embodiment guide.
Figure 6:
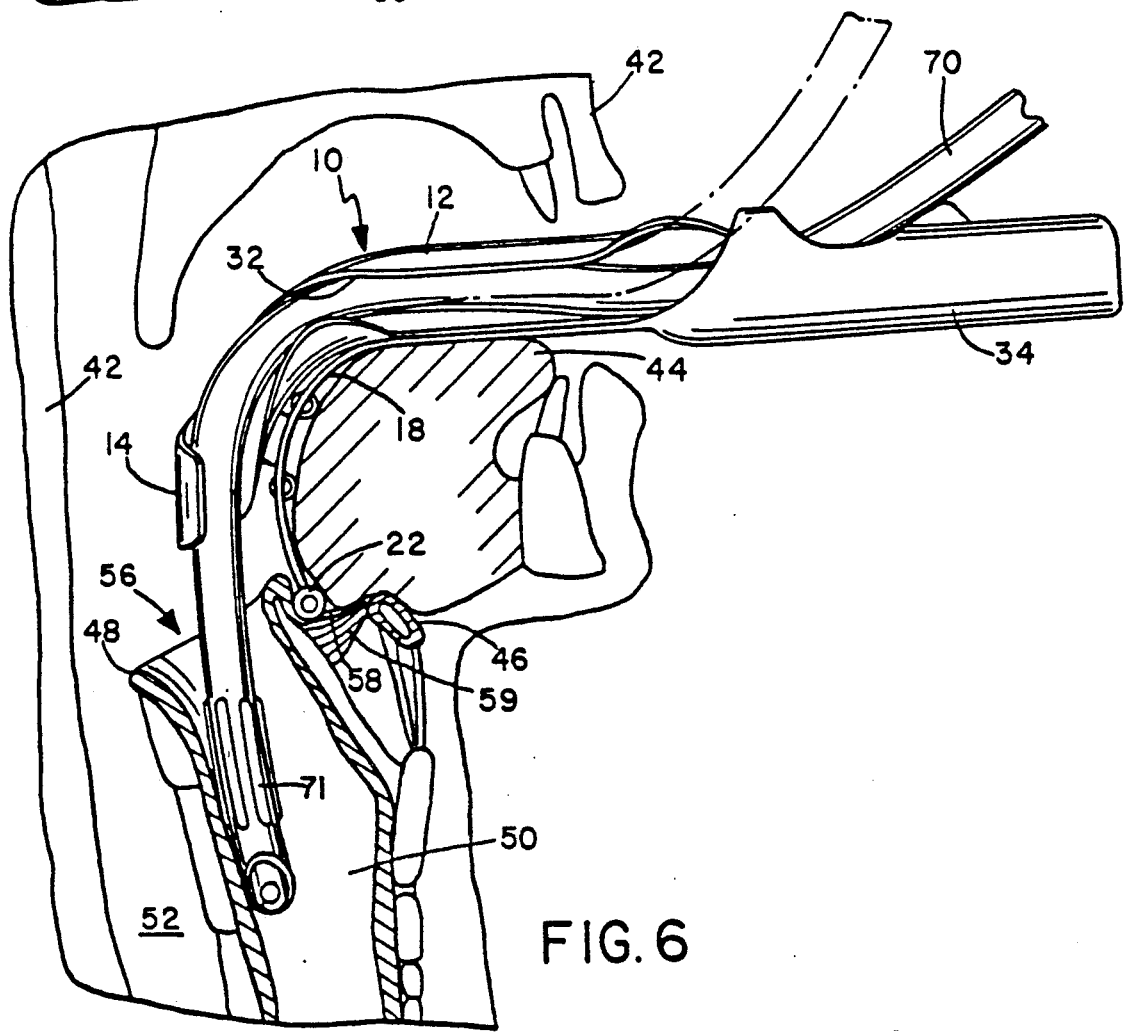
FIG. 6 is a similar view of the end of the first embodiment guide seated over the hyo-epiglottic ligament and the endotracheal tube inserted through the first embodiment guide into the trachea.

The method of inserting an endotracheal tube using the tracheal intubation guide according to the principles of the invention will best be understood with reference to FIGS. 5 and 6 of the drawings, which show a partial section through the head 42 of a patient. As shown in FIGS. 5 and 6, the tongue 44 curves downwardly at the back of the throat where the root of the tongue is anchored to the hyoid bond 46. The hyoid bone is a U-shaped structure which lies horizontally and opens rearwardly, and which surrounds and suspends the larynx 48. The larynx 48 is the upper end of the windpipe, or trachea 50. To the rear of the trachea is the esophagus 52 through which food and drink enters the stomach. The epiglottis 54 is a shield-shaped cartilage which rises above the glottis 56, or opening to the windpipe, and which protects the larynx. When food and drink is passed over the tongue toward the windpipe, it is deflected around the lateral aspects of the glottis and is thus prevented from entering the larynx, which is also protected by the reflex closure of the vocal cords. The epiglottis 54 is anchored anteriorly to the hyoid bone via the hyo-eliglottic ligament 59. The depression 58 which is bounded anteriorly by the tongue, posteriorly by the epiglottis and inferiorly by the hyo-epiglottic ligament is known as the vallecula. In a coronal section, the depression 58 assumes a convex contour between the epiglottis and the hyoid bone over the hyo-epiglottic ligament. Anterior traction at the base of the tongue moves the hyoid bone anteriorly, which tensions the hyo-epiglottic ligament and thus elevates the epiglottis forwardly and off the glottis to expose the opening to the larynx.

Figure 3:
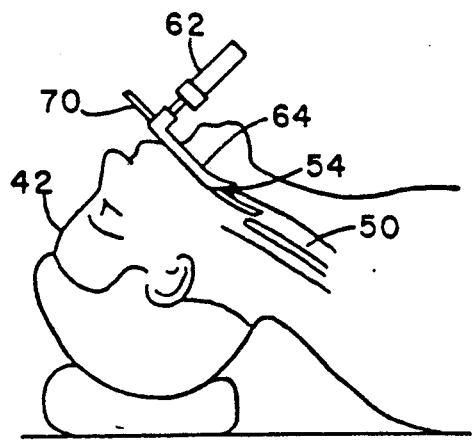
FIG. 3 illustrates a prior art method of inserting an endotracheal tube with the head tilted back.

Before describing the technique of inserting an endotracheal tube according to this invention, reference is first made to FIG. 3 which illustrates a prior art technique using a laryngoscope 62 for direct observation of the tube insertion. The laryngoscope 62 must first be inserted as shown in FIG. 3, requiring the patient's head to be tilted back. In view of the risk of additional spinal cord injury resulting from such head movement, this technique is not normally used for trauma victims. The tip of the laryngoscope blade 64 elevates the epiglottis.

The guide of the invention allows relatively accurate, "blind" insertion of an endotracheal tube without needing to tilt or move a patient's head. As illustrated by use of the first embodiment of the guide illustrated in FIGS. 1 and 2, before insertion of the guide, an endotracheal tube 70 having a cuff 71 adjacent its forward end is first inserted from the rear to the forward end of tubular member 12, into the position shown in FIG. 4. With the head in the position shown in FIG. 4, the mouth is opened and the forward end of the guide is inserted through the mouth, as indicated by the arrow in FIG. 5. The guide surface slides over the tongue surface into the throat, assisted by the rollers which ensure relatively smooth movement even in cases where the tongue surface is sticky. The guide is inserted into the throat by the operator gripping the handle as shown in FIG. 2, until the forward edge of the guide surface engages the front of the epiglottis as shown in FIG. 6. As can be seen in FIG. 6, the curvature of the guide tube and anterior guide surface is designed to follow the curvature of the back of the tongue into the throat.

If the guide is centrally positioned, the concave indent at the forward edge of the guide surface will seat or fit over the convex contour of the hyo-epiglottic ligament, as shown in FIG. 6, with one of the rollers on each side of the ligament. Correct positioning can be detected by external palpation of the sides of the neck in the region of the hyoid bone. If the guide is not accurately seated on the ligament, a lateral edge of the guide will be felt on one side of the neck above the hyoid bond. In that case, the guide is partially withdrawn and then re-inserted. When the guide is accurately seated, lateral movement of the guide will result in a generalized movement of the hyoid bone, which can be detected by external palpation of the neck.

Once accurate positioning of the guide has been detected, anterior elevation of the tongue will tension the hyo-epiglottic ligament and elevate the epiglottis anteriorly, as indicated in FIG. 6, opening the larynx immediately behind the epiglottis. The guide is designed so that when the epiglottis is elevated, the open forward end of the guide tube and the end of the previously inserted endotracheal tube will be positioned directly opposite the opening into the trachea, as shown in FIG. 6.

The epiglottis may be elevated by elevation of the tongue. However, the guide may itself include an epiglottic elevating ramp (not shown in the drawings) in an alternative embodiment, although this is not essential for proper functioning of the guide. The ramp may suitably comprise a one-inch member hinged to the rear of the guide surface approximately one inch from its forward edge and designed to hand down at a 45-degree angle during insertion of the guide. The ramp will be connected to a lever on the handle. When the guide has been positioned, the lever may be used to elevate the ramp anteriorly and pinch the epiglottis between the ramp and rear of the guide surface. This would show that the epiglottis had been located and would also ensure maximum opening of the larynx.

Once accurate positioning of the guide has been assured and the epiglottis has been elevated, the endotracheal tube 70 is advanced through the tubular member 12 as shown in FIG. 6, which guides it down through the larynx and into the trachea. Once the tube 70 has been inserted fully, cuff 71 is inflated to hold the tube in place and the guide can be removed leaving the tube in place. The open section, serpentine groove in the tubular guide member, will keep the tube within the member 12 during positioning but allows the guide 10 to be removed easily without dislodging the tube 70 once the tube has been inserted, as indicated by the dotted lines in FIG. 6. Once tube 70 is moved to the position shown in dotted lines, the guide 10 can be easily withdrawn.

Figure 4:
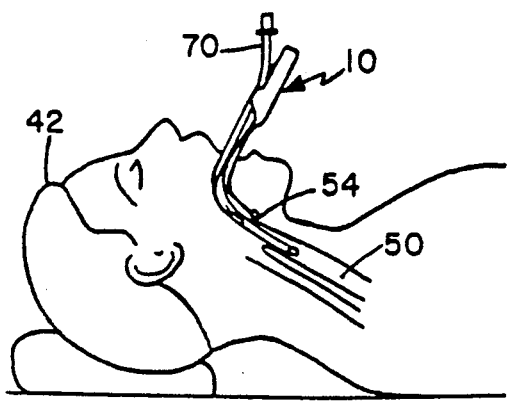
FIG. 4 illustrates the method of inserting an endotracheal tube according to the principles of the invention.

Although in the method described above, an endotracheal tube is positioned in the tubular member prior to insertion into the throat in view of the open, serpentine cut-out, it may alternatively be positioned after the guide 10 has been inserted, depending on the shape and position of the serpentine cut-out. For example, the intubation guide may be designed to have an opening in its posterior surface at the forward end, facing the nasal pharynx, to allow entry of a nasally inserted endotracheal tube into the guide member 12, for final guiding of the endotracheal tube into the trachea. However, the insertion technique will normally be via the mouth, as indicated in FIGS. 4 to 6.

Figure 7:
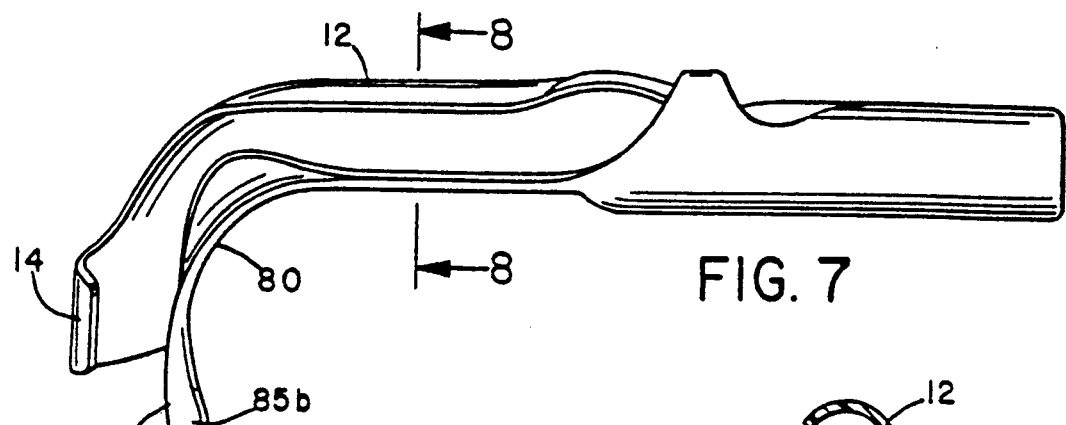
FIG. 7 is a perspective view of a tracheal intubation guide according to a second embodiment of the invention.
Figure 8:
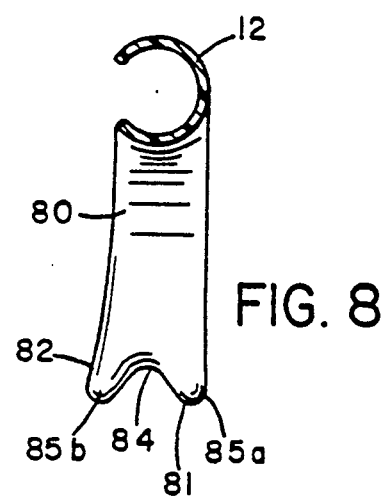
FIG. 8 is a sectional view showing the profile of the anterior guide surface of the second embodiment.
Figure 9:
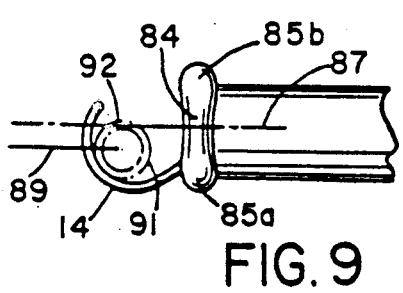
FIG. 9 is an end view of FIG. 7, rotated by 90° to illustrate the alignment of the forward end with the anterior guide surface.
Figure 10:
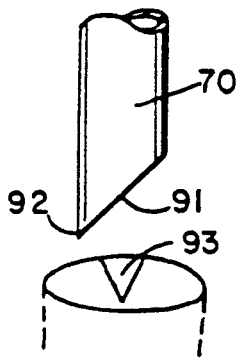
FIG. 10 is a schematic illustration of the alignment of the beveled tip of an endotracheal tube without an offset between the center lines of the forward end and the anterior guide surface.
Figure 11:
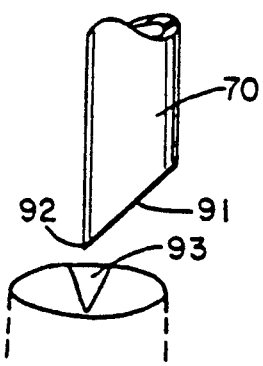
FIG. 11 is a schematic illustration f the alignment of the beveled tip when the center lines are offset.

A second embodiment of the guide is illustrated in FIGS. 7-9. The second embodiment is characterized primarily in that the anterior guide surface has a smooth, continuous surface unbroken by the rollers of the first embodiment. Thus, as with the first embodiment, the guide surface is attached to the underside of the through bore and extends beyond the curved forward end 14 of the guide tube 12. The guide surface of the second embodiment is indicated by reference numeral 80. As illustrated, the guide surface 80 extends beyond the forward end of 14 and includes a forward edge 81 having a generally concave shape 84 lying between a pair of curved projections 85a and 85b. As best seen in FIG. 9, the anterior guide surface has a center line 87 which bisects the concave indentation 84 and the forward edge 81. In addition, the forward end 14 of the guide tube has a center line 89 which is offset laterally from the center line 87. As is known, the distal tip of the endotracheal tube 70 is normally beveled, with the bevel being indicated by reference numeral 91, looking down on the tube from above in FIGS. 10 and 11. If the center lines of the forward end 14 and the anterior guide surface of either of the above-described embodiments were co-linear, the engagement of the hyo-epiglottic ligament would result in an alignment between the beveled end 92 and the opening between the vocal cords 93, in the larynx, as illustrated in FIG. 10. In FIG. 10, the tip of the bevel 92 is offset from the center of the opening between the vocal cords 93, which might result in the bevel tip snagging on a vocal cord, preventing its entrance into the trachea. On the other hand, with the offset between center lines illustrated in FIG. 11, the distal end of the tube 70 is aligned with the center line of the forward end 14. However, the tip 92 of the bevel is now aligned substantially with the center line of the guide surface, and, therefore, with the center line of the vocal cord opening 93 in the larynx. This alignment increases the likelihood of the bevel tip 92 entering and guiding the distal end of the endotracheal tube 70 through the vocal cords and into the trachea.

The guide and insertion technique described above allows an endotracheal tube to be inserted "blind" relatively easily and dependably. The technique does not require potentially damaging movement of the patient's neck or direct observation of the larynx, which may be obscured through blood, vomitus, or other foreign matter which may be in the pharynx of trauma and cardiac arrest victims. Thus, a tube can be inserted relatively quickly and reliably into the trachea to secure a patient's airway and assure adequate ventilation.

Figure 12:
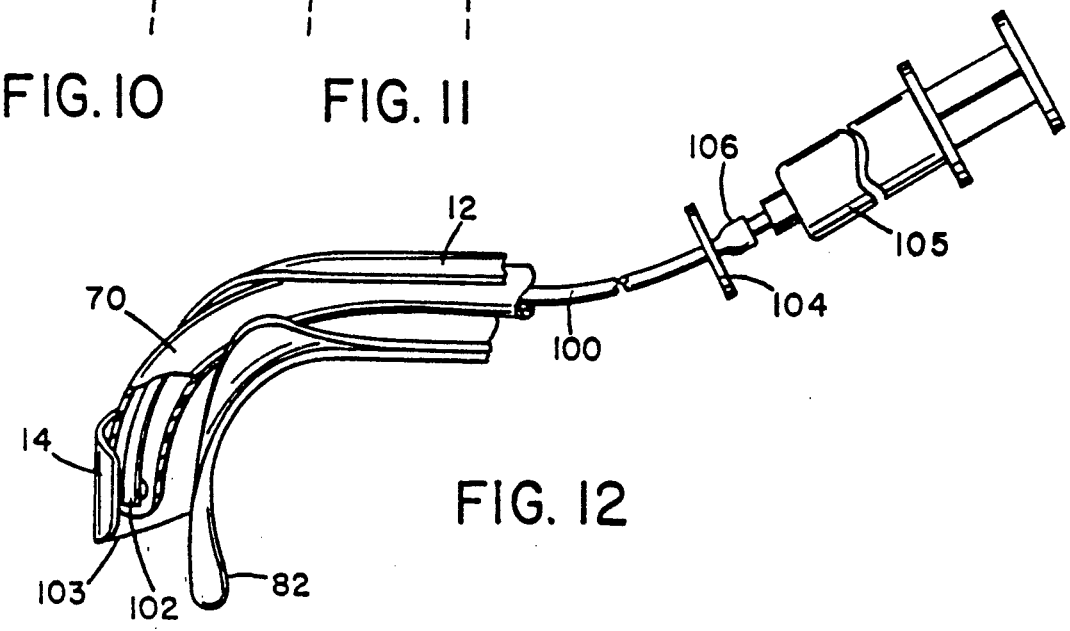
FIG. 12 is an illustration of a small tube inserted in the endotracheal tube for introducing a local anesthetic during intubation.

A small catheter 100, such as is illustrated in FIG. 12, may be provided to extend from the rear to the forward end of the guide, with a nozzle 102 at its forward end 103. A slidable stop 104 retains the proximal end of the catheter 100 at the rear end of the tube 12. This can be used with a syringe 105 of local anesthetic attached to the rear end 106 of the catheter 100. The catheter 100 is fed into the tube 70, and the guide, with the tube 70 in place, is advanced into a patient's throat. When the anesthetic is released into the catheter, it sprays ahead of the guide out the nozzles to anesthetize the tongue and larynx with local anesthetic. This can aid in inserting the guide and endotracheal tube in patients who are awake.

Refer now to FIGS. 13-17 for an understanding of the third embodiment of the tracheal intubation guide of this invention and a method of intubation assisted by the third embodiment, by which correct positioning of the guide is determined by a palpable displacement of the hyoid bone.

Figure 13:
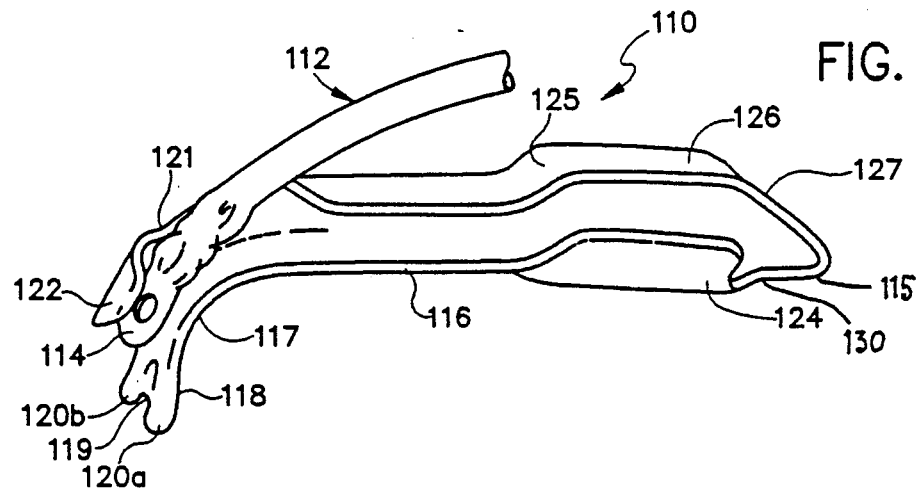
FIG. 13 is a side view of a tracheal intubation guide according to a third embodiment of the invention.
Figure 14:
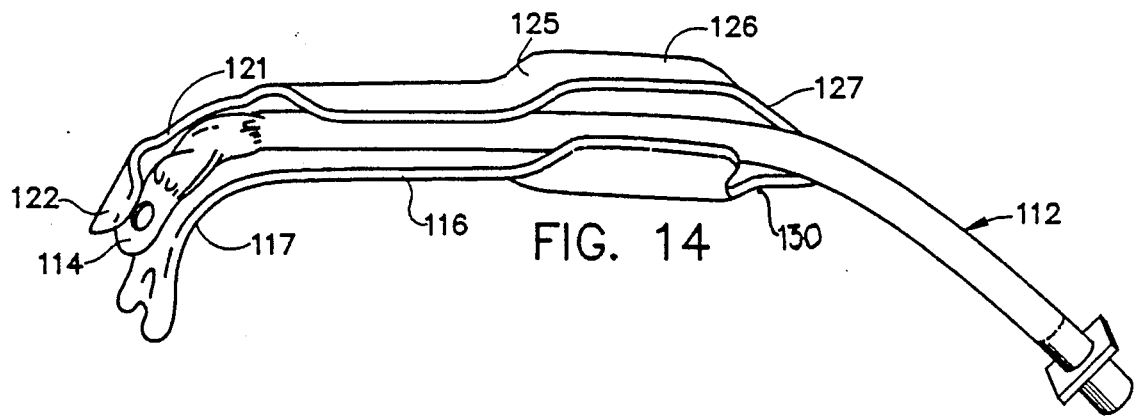
FIG. 14 is a view, similar to that of FIG. 7, with a tracheal tube held in the tracheal intubation guide.
Figure 15:
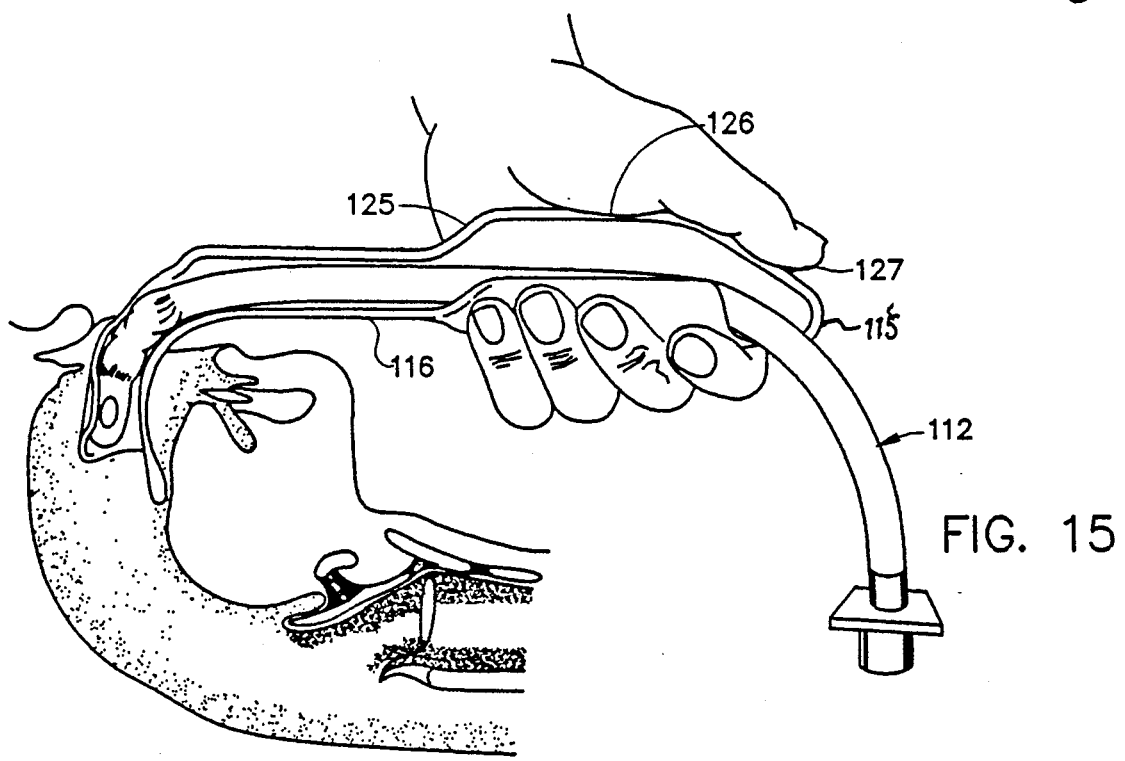
FIG. 15 is a sectional view showing the profile of neck anatomy of a patient being intubated with the assistance of the third embodiment of the tracheal intubation guide.

With reference now to FIGS. 13-15, the third embodiment of the invention includes a tracheal intubation guide 110 which assists intubation of a patient by a tracheal tube 112 having a tip 114. The guide 110 has a proximal end 115, an elongate proximal section 116, which transitions to a curved section 117, and then to a distal end 118. The distal end 118 includes a blade edge which has a hyo-epiglottic engagement indentation 119 and a pair of bulbous protuberances 120a and 120b on respective sides of the indentation 119. The third embodiment of the guide 110 has a tube-accepting opening which extends along its entire length and which widens at 121 in the vicinity of the curved section 117. The widening 121 narrows distally by way of a flange 122. Proximally, a retention flange 124 projects upwardly from the anterior guiding surface (not shown) on the bottom of the guide 116.

The tube 112 is inserted and held in the guide 110 as illustrated in FIGS. 14 and 15, the tip 114 being retained by the flange 122, and the rest of the tube by the flange 124.

The best location for manipulation of the tracheal intubation guide 110 is from the head or side of a patient to be intubated, as illustrated in FIG. 15. In order to provide the best response to manipulation, the tracheal intubation guide 110 has a proximal grasping portion including an upwardly ramped surface 125, a palm-supporting surface 126, and a downwardly-ramp thumb supporting surface 127. An indentation 130 at the proximal end of the guide behind the flange 124 permits the tube 112 to extend out through the proximal end of the guide 110. As FIGS. 13 and 15 illustrate, the flange 124 also provides a finger-grasping surface so that a practitioner's hand can grasp and manipulate the intubation guide 110 prior to and during intubation.

The widening 121 of the opening in the guide 110 is opposite the curved section of the guide anterior surface; this opening allows the guide 110 to be easily removed without lateral displacement of the tube 112, once the tube is positioned and seated in the trachea.

In all other respects, the third embodiment of the guide, illustrated in FIGS. 13-15, is identical with the second embodiment of the guide described above.

Figure 16:
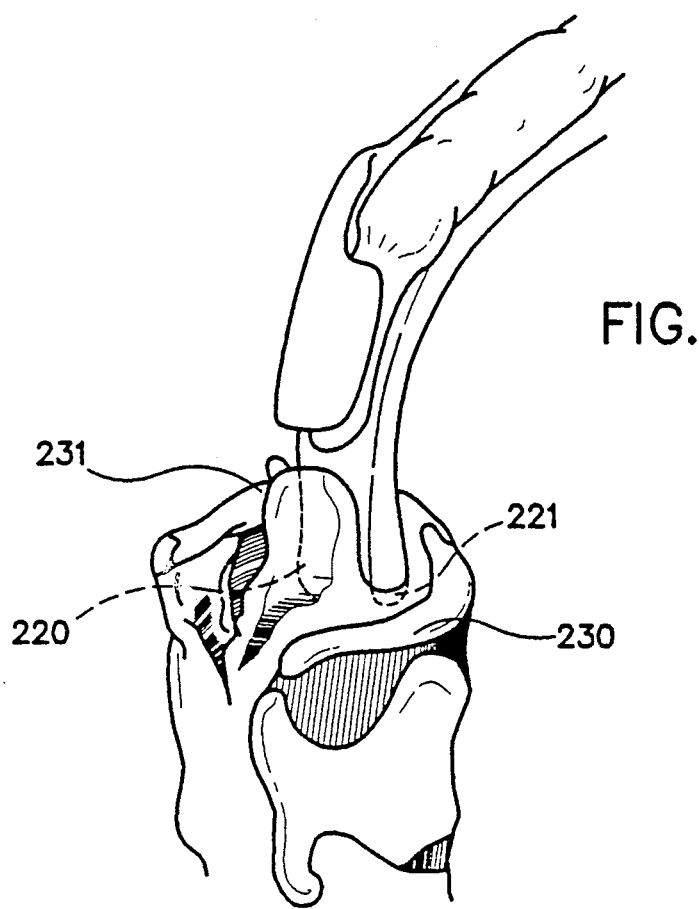
FIG. 16 is a perspective view illustrating engagement of vallecular anatomy by the blade end of the third embodiment tracheal intubation guide.
Figure 17:
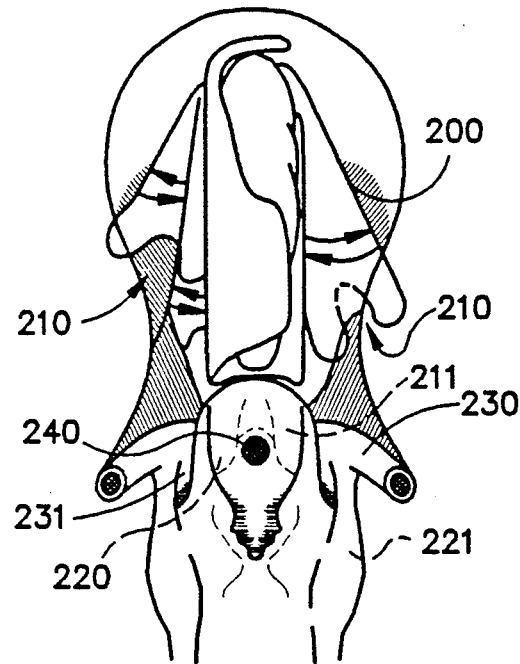
FIG. 17 is a view similar to that of FIG. 16, but rotated by approximately 45 degrees, with the viewer positioned at the back of the throat of a patient being intubated.

The third embodiment of the guide supports an improved method for tracheal intubation in which accurate seating of the guide for intubation is indicated by elevation of the hyoid bone. The method is illustrated in FIGS. 15-17. In FIG. 17, the viewer is positioned at the back of the throat and looks out over the top surface 200 of the tongue through the oral opening. As described above for the second embodiment, the distal end 210 of the third embodiment of the tracheal intubation guide is advanced over the back surface of the tongue toward the vallecular anatomy. Preferably, the distal end 210 is advanced with a lateral sweeping motion as shown in FIG. 17 in a search maneuver. As the distal end 210 advances toward the vallecular anatomy, the hyo-epiglottic indentation 211 in the distal blade edge of the guide, when properly positioned, seats on the hyo-epiglottic ligament 240. The ligament 240 is straddled by the bulbous protubrances 220 and 221 on the distal end of the guide. When the distal end is properly seated, the bulbous protubrances 220 and 221 engage underneath the hyoid bone 230, which is positioned in front of the epiglottis 231.

The method of intubation by means of the third embodiment of the tracheal intubation guide is practiced first by lubrication of the tracheal tube 112 and insertion into the guide 110 so that the tip 114 of the tube is flush with the leading edge of the tip retaining flange 122 on the distal portion of the guide. With the head and neck of a patient in a neutral position, the distal end is advanced over the patient's tongue in the searching motion until a significant resistance is encountered. At this point, the distal end is seated in the patient's vallecular anatomy against the hyo-epiglottic ligament, with the tongue against the anterior surface and the epiglottis against the posterior surface of the distal end of the guide. Repeating prior disclosure, the hyo-epidlottic ligament provides a midline structural connection between the midline of the U-shaped hyoid bone and the epiglottis, and is centered within the U of the hyoid bone. This is clearly illustrated in FIG. 17. The hyo-epiglottic ligament is in the same plane as the hyoid bone. The indentation 211 of the distal end of the guide receives the hyo-epiglottic ligament 240, while the lateral bulbous protubrances 220 and 221 extend forward beyond the plane of the hyoid bone/hyo-epiglottic ligament structure to engage, or wedge under and within, the U of the hyoid bone 230.

Because of the hyo-epiglottic indentation in the distal blade edge and the bulbous lateral protubrances which bracket the indentation and which distinctively engage under the hyoid bone, proper positioning of the third embodiment of the guide with respect to the larynx can be accurately assessed through the external surface of a patient's neck. When the practitioner is advancing the guide into position with one hand, the hyoid bone is palpated through the external surface of the neck with the other hand. As the lateral bulbous protubrances of the guide distal end engage under the hyoid bone, a distinctive elevation of the bone can be felt by the practitioner's fingers on the external surface of the neck. Finally, positive engagement of the guide can be verified by moving the proximal end of the guide laterally, side to side, in response to which, the distal end of the guide will move laterally. If the bulbous protubrances are properly engaged under the hyoid bone, distinctive lateral movement of the entire hyoid bond can be felt on the external surface of the neck. Conversely, if the guide is not properly engaged under the hyoid bone, the operator will not feel the distinctive elevation or the lateral movements of the bone. In this case, repositioning will be required before tracheal tube advancement.

Upon verification of accurate positioning of the guide by external palpation of the hyoid bone, slight forward or caudad pressure on the guide will stretch the hyo-epiglottic ligament around the distal end of the guide. This elevates the epiglottis tightly up against the proximal surface of the guide. In this position, the open glottis is directly opposing the tip of the tracheal tube. The tracheal tube can then be blindly advanced into the open glottis. The tracheal tube is removed from the guide through the opening in the guide and the guide is removed from the patient's mouth, leaving the tube in place. Verification of proper tube positioning and placement must then be accomplished by prior art techniques, such as, asculation of breath sounds or carbon dioxide detection.

Although three preferred embodiments of the invention has been described above by way of example, it will be understood by those skilled in the field that modifications may be made to the disclosed embodiments without departing from the scope of the invention, which is defined by the appended claims.

I claim:

1. A tracheal intubation guide for facilitating insertion of a tube into the trachea of a patient, comprising:
   a tubular member with a proximal end and a distal end, said tubular member having a substantially straight proximal section including said proximal end, a distal section including said distal end, and a curved section joining said proximal and distal sections;
   a blade edge in said distal end;
   a centering, hyo-epiglottic engagement indentation in said blade edge; and
   a pair of bulbuous hyoid engagement projections on said blade edge, each of said bulbuous projections displaced in a respective lateral direction from said indentation.

2. The tracheal intubation guide of claim 1, further including:
   an anterior tongue-engagement surface extending along said elongate tubular member; and a continuous tube disengagement opening in said tubular member extending from said distal end to said proximal end, said tube disengagement opening including a portion in said curved section which opens opposite said tongue-engagement surface.

3. The tracheal intubation guide of claim 2, further including:
a finger engagement surface on said proximal end, which joins said tongue-engagement surface; and
a thumb engagement surface on said proximal end separated by said tube disengagement opening from said finger engagement surface.

4. The tracheal intubation guide of claim 1, further including:
a finger engagement surface on said proximal end, which joins said tongue-engagement surface; and
a thumb engagement surface on said proximal end separated by said tube disengagement opening from said finger engagement surface.

5. The tracheal intubation guide of claim 1, further including a tube-tip retaining flange in said distal end, which projects into said tube-disengagement opening.

6. An instrument for external palpation of the neck of a patient, comprising:
an elongate member with a proximal portion and a distal extension;
an anterior, tongue engaging guide surface extending along part of said elongate member from said distal extension to said proximal portion;
a vallecular engagement edge on said distal extension;
a hyo-epiglottic ligament engagement indentation in said vallecular engagement edge; and
hyoid engagement means on said vallecular engagement edge for hyoid bone engagement.

7. The instrument of claim 6, further including:
a grasping means on said proximal portion for inducing lateral movement of said distal extension upon engagement by said hyoid engagement means of the hyoid bone.

8. A method for intubation of a patient's trachea, said method practiced by means of a tracheal intubation guide with a distal end, a proximal end, a curved anterior surface, means for releasably retaining a tube, and hyoid engagement means on said distal end for hyoid bone engagement, said method including the steps of:
first, inserting a tube in said tracheal intubation guide;
then, inserting said tracheal intubation guide, distal end first, into a patient's mouth so that the guide surface follows the rear surface of the tongue into the throat; and
advancing the tracheal intubation guide until the hyoid engagement means engages the hyoid bone;
followed by, detecting accurate positioning of the tracheal intubation guide by palpating the sides of the neck to determine whether the hyoid bone has been elevated.

9. The method of claim 8, further including the steps of:
applying lateral motion to the tracheal intubation guide at the proximal end; and
palpating the sides of the neck to determine whether the hyoid bone is moved laterally.

10. The method of claim 9, further including the steps of:
elevating the epiglottis anteriorly to open the larynx;
guiding the tube into the trachea; and
removing the tracheal intubation guide from the tube and the patient's mouth.

* * * * *